(12) United States Patent
Jung et al.

(10) Patent No.: US 8,580,506 B2
(45) Date of Patent: Nov. 12, 2013

(54) METHOD AND COMPOSITION FOR ENHANCING EFFICIENCY AND SENSITIVITY IN POLYMERASE CHAIN REACTION

(75) Inventors: Sun-ok Jung, Seongnam-si (KR); Hee-kyun Lim, Hwaseong-si (KR); Kyu-youn Hwang, Yongin-si (KR); Joon-ho Kim, Seongnam-si (KR); Sung-hong Kwon, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 209 days.

(21) Appl. No.: 13/069,969

(22) Filed: Mar. 23, 2011

(65) Prior Publication Data
US 2012/0064576 A1    Mar. 15, 2012

(30) Foreign Application Priority Data
Sep. 14, 2010 (KR) .................. 10-2010-0089922

(51) Int. Cl.
*C12Q 1/68* (2006.01)
*C12P 19/34* (2006.01)

(52) U.S. Cl.
USPC ................. 435/6.12; 435/6.1; 435/6.11

(58) Field of Classification Search
None
See application file for complete search history.

(56) References Cited

U.S. PATENT DOCUMENTS

| | | | |
|---|---|---|---|
| 6,218,153 B1 | 4/2001 | Sklar et al. | |
| 6,491,008 B1 | 12/2002 | Zubeck | |
| 7,262,006 B1 | 8/2007 | Belly et al. | |
| 7,727,718 B2 | 6/2010 | Chomczynski | |

OTHER PUBLICATIONS

Agarwal, R.K. et al., PCR amplification of highly GC-rich DNA template after denaturation by NaOH, Nucleic Acids Res., 1993; 21(22): 5283-5284.
Wang, H. et al., A simple method of preparing plant samples for PCR, Nucleic Acids Res., 1993; 21(17): 4153-4154.
Mackay et al., "Real-Time PCR in Virology," *Nucleic Acids Research*, 30(6): 1292-1305 (2002).

*Primary Examiner* — Young J Kim
(74) *Attorney, Agent, or Firm* — Leydig, Voit & Mayer, Ltd.

(57) ABSTRACT

Methods and compositions for enhancing reaction efficiency and sensitivity in polymerase chain reaction (PCR) are disclosed.

9 Claims, 8 Drawing Sheets

```
                         SEQUENCE LISTING

<160> NUMBER OF SEQ ID NOS: 8

<210> SEQ ID NO 1
<211> LENGTH: 442
<212> TYPE: DNA
<213> ORGANISM: Staphylococcus aureus
<220> FEATURE:
<221> NAME/KEY: gene
<222> LOCATION: (1)..(442)
<223> OTHER INFORMATION: Sa442 fragment

<400> SEQUENCE: 1
gatcaatctt tgtcggtaca cgatattctt cacgactaaa taaacgctca ttcgcgattt      60
tataaatgaa tgttgataac aatgttgtat tatctactga aatctcatta cgttgcatcg     120
gaaacattgt gttctgtatg taaaagccgt cttgataatc tttagtagta ccgaagctgg     180
tcatacgaga gttatatttt ccagccaaaa cgatattttt ataatcatta cgtgaaaaag     240
gtttcccttc attatcacac aaatatttta gcttttcagt ttctatatca actgtagctt     300
ctttatccat acgttgaata attgtacgat tctgacgcac catcttttgc acacctttaa     360
tgttatttgt tttaaaagca tgaataagtt tttcaacaca acgatgtgaa tcttctaaga     420
agtcaccgta aaatgaagga tc                                              442

<210> SEQ ID NO 2
<211> LENGTH: 687
<212> TYPE: DNA
<213> ORGANISM: Staphylococcus aureus
<220> FEATURE:
<221> NAME/KEY: gene
<222> LOCATION: (1)..(687)
<223> OTHER INFORMATION: Nuc fragment

<400> SEQUENCE: 2
atgacagaat acttattaag tgctggcata tgtatggcaa ttgtttcaat attacttata      60
gggatggcta tcagtaatgt ttcgaaaggg caatacgcaa agaggttttt cttttttcgct    120 actagttgct tagtgttaac tttagttgta gtttcaagtc taagtagctc agcaaatgca    180
tcacaaacag ataacggcgt aaatagaagt ggttctgaag atccaacagt atatagtgca    240
acttcaacta aaaaattaca taaagaacct gcgacattaa ttaaagcgat tgatggtgat    300
acggttaaat taatgtacaa aggtcaacca atgacattca gactattatt agttgataca    360
cctgaaacaa agcatcctaa aaaaggtgta gagaaatatg gccctgaagc aagtgcattt    420
acgaaaaaaa tggtagaaaa tgcaaataaa attgaagtcg agtttgacaa aggtcaaaga    480
```

-continued

```
actgataaat atggacgtgg cttagcgtat atttatgctg atggaaaaat ggtaaacgaa      540
gctttagttc gtcaaggctt ggctaaagtt gcttatgttt ataaacctaa caatacacat      600
gaacaacttt taagaaaaag tgaagcacaa gcgaaaaaag agaaattaaa tatttggagc      660
gaagacaacg ctgattcagg tcaataa                                          687
```

```
<210> SEQ ID NO 3
<211> LENGTH: 22
<212> TYPE: DNA
<213> ORGANISM: Artificial Sequence
<220> FEATURE:
<223> OTHER INFORMATION: Forward primer for Sa442

<400> SEQUENCE: 3
gttgcatcgg aaacattgtg tt                                                22

<210> SEQ ID NO 4
<211> LENGTH: 27
<212> TYPE: DNA
<213> ORGANISM: Artificial Sequence
<220> FEATURE:
<223> OTHER INFORMATION: Reverse primer for Sa442

<400> SEQUENCE: 4
atgaccagct tcggtactac taaagat                                           27

<210> SEQ ID NO 5
<211> LENGTH: 20
<212> TYPE: DNA
<213> ORGANISM: Artificial Sequence
<220> FEATURE:
<223> OTHER INFORMATION: Sa442 Taqman probe

<400> SEQUENCE: 5
tgtatgtaaa agccgtcttg                                                   20

<210> SEQ ID NO 6
<211> LENGTH: 23
<212> TYPE: DNA
<213> ORGANISM: Artificial Sequence
<220> FEATURE:
<223> OTHER INFORMATION: Forward primer for nuc fragment

<400> SEQUENCE: 6
tgcgacatta attaaagcga ttg                                               23

<210> SEQ ID NO 7
<211> LENGTH: 24
<212> TYPE: DNA
<213> ORGANISM: Artificial Sequence
<220> FEATURE:
<223> OTHER INFORMATION: Reverse primer for nuc fragment

<400> SEQUENCE: 7
gtctgaatgt cattggttga cctt                                              24

<210> SEQ ID NO 8
<211> LENGTH: 18
<212> TYPE: DNA
<213> ORGANISM: Artificial Sequence
<220> FEATURE:
<223> OTHER INFORMATION: nuc Taqman probe

<400> SEQUENCE: 8
tggtgatacg gttaaatt                                                     18
```

METHOD AND COMPOSITION FOR ENHANCING EFFICIENCY AND SENSITIVITY IN POLYMERASE CHAIN REACTION

CROSS-REFERENCE TO RELATED APPLICATIONS

This application claims priority to Korean Patent Application No. 10-2010-0089922, filed on Sep. 14, 2010, and all the benefits accruing therefrom under 35 U.S.C. §119, the disclosure of which is incorporated herein in its entirety by reference.

BACKGROUND

1. Field

The present disclosure relates to methods and compositions for enhancing reaction efficiency and sensitivity in polymerase chain reaction (PCR).

2. Description of the Related Art

The number of diseases known to be caused by pathogenic microorganisms or genetic variations is increasing. For the case of rapidly progressing diseases, a precise and speedy diagnosis is desirable. For the case of diseases caused by microorganisms, the ability to detect even a trace amount is desirable because microorganism proliferation rates are high. Various methods using polymerase chain reaction (PCR) have been developed and used for early diagnosis or detection of such diseases. In particular, PCR is useful because results are obtained from a trace amount of a sample within a short time period. PCR methodology has been developed in various ways to improve detection efficiency and sensitivity. However, higher accuracy and sensitivity of PCR requires longer reaction time and higher cost. Each cycle in PCR consists of denaturation, annealing, and extension steps. In order to enhance the accuracy and sensitivity of PCR, each step in each cycle must be performed for sufficient time; and a modified polymerase is used to minimize non-specific reactions caused by the polymerase, leading to increased costs, or alternatively, a pre-activation time is added, increasing total reaction time. In addition, use of a sophisticated, high-performance apparatus leads to high costs in PCR. Depending on the sequences or structures of the primers used in PCR, annealing may occur between the primers, and as amplification proceeds, primer dimers may be generated. The primer dimers are one of the major reasons for reduction in the specificity and efficiency of PCR. Since generation of primer dimers competes with amplification of the target sequence, amplification efficiency may be significantly reduced. Generation of primer dimers may be prevented by enhancing stringency via control of the amount of salts, such as $MgCl_2$, in the PCR reaction solution, or by using a "hot start" polymerase, e.g., hot start Taq. However, by doing so, PCR efficiency may be reduced or the total reaction time may be prolonged.

Accordingly, there is still a need to develop a PCR method capable of quickly and accurately detecting a trace amount of a target material in a sample.

SUMMARY

Provided are methods of enhancing reaction efficiency and sensitivity in polymerase chain reaction (PCR). In an embodiment, the method includes preparing a biological sample and a mixture for PCR, adding alkali to at least one of the biological sample and the mixture for PCR, mixing the biological sample and the mixture for PCR to prepare a reaction solution for the PCR, and performing the PCR on the reaction solution for PCR.

Provided are methods of suppressing generation of primer dimers in PCR.

Provided are compositions for high-efficiency and high-sensitivity PCR. In an embodiment, the composition includes alkali and a mixture for PCR.

BRIEF DESCRIPTION OF THE DRAWINGS

These and/or other aspects of the invention will become apparent and more readily appreciated from the following description of exemplary embodiments, taken in conjunction with the accompanying drawings of which.

DETAILED DESCRIPTION

Figure 1A:
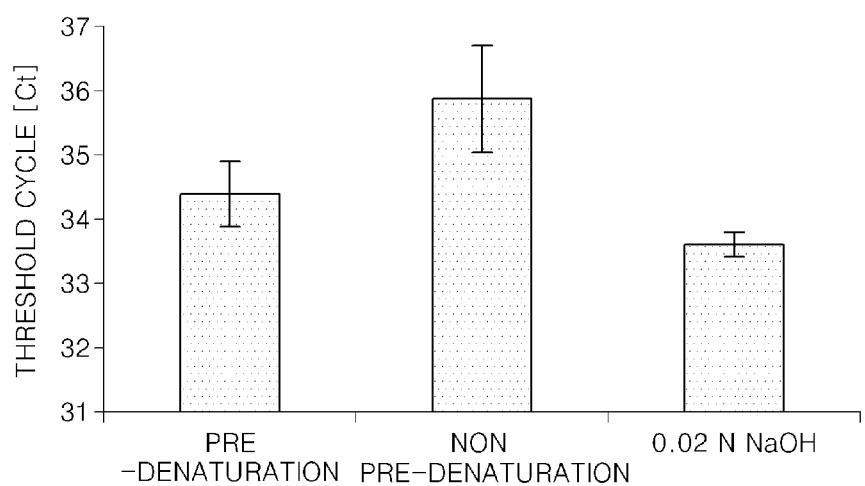
FIG. 1A is a histogram showing threshold cycle (Ct) values for PCR performed with pre-denaturation, no pre-denaturation, and addition of 0.02N NaOH, respectively.

Reference will now be made in detail to embodiments of the invention, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

An aspect of the present invention provides a method of enhancing a reaction efficiency and sensitivity of polymerase chain reaction (PCR), in which the method includes preparing a biological sample and a mixture for PCR and adding alkali to at least one of the biological sample and the mixture for PCR, mixing the biological sample and the mixture for PCR to prepare a reaction solution for PCR, and performing PCR on the reaction solution.

PCR is a technique to amplify the number of copies of a target nucleic acid by several orders of magnitude. PCR is performed by repeating a cycle that generally consists of denaturation of a target nucleic acid (template) into single strands, annealing primers to the denatured template, and extension of the primers annealed to the template by a polymerase an appropriate number of times to detect amplified products.

The term "reaction sensitivity" or "limit of detection (LOD)" used herein refers to the minimum amount or copy number of target nucleic acid that is reliably detected and quantified by polymerase chain reaction (PCR) under a given set of PCR conditions. In regard to real time-PCR (RT-PCR), the limit of detection is represented as the threshold cycle (Ct) value. For RT-PCR performed using fluorescent reporter labels, the Ct value is defined as the cycle number at which the fluorescence signal begins to significantly increase compared to the background signal.

The term "reaction efficiency" used herein refers to the average number of doublings of a target nucleic acid/cycle of PCR under a given set of conditions. PCR efficiency is affected by various factors including the purity of the sample, the amount of target nucleic acid, the reaction conditions, and the presence of reaction inhibitors. As reaction efficiency is increased, amplification may reach a detectable level in a shorter time period. For example, PCR efficiency may be interpreted as the time period required for performing the entire number of cycles, that is, the time period spent to complete the number of cycles required to amplify a target nucleic acid to a detectable level.

The term "mixture for PCR" used herein refers to a mixture including all components for performing PCR other than a template and forward and reverse primers for the template, and may also be referred to as a "master mix" or a "pre mix." Typically, a mixture for PCR includes a buffer solution for the polymerase reaction, such as 10 mM Tris HCl, pH 8.0 to 9.0, 40 mM KCl, 1.5 mM $MgCl_2$, 250 μM each dNTP, and 0.5 to 1 U of a DNA polymerase. In some embodiments, the mixture for PCR also includes a forward primer and a reverse primer. The concentration of the forward and reverse primers in the mixture for PCR can be 0.01 μM to 5 mM. The mixture for PCR may be formulated at a high concentration, such as at a concentration of ×2 to ×10 of the final concentration of components in the reaction solution for PCR, so that the mixture for PCR can be diluted appropriately to achieve the desired final concentration of components in the reaction solution for PCR.

The term "reaction solution for PCR" used herein refers to a reaction solution that includes all the components for performing PCR, including the template and forward and reverse primers. The concentration of the forward and reverse primers can be 0.01 μM to 5 mM.

According to an embodiment of the present invention, the biological sample may be cells, body fluids, or nucleic acids derived from mammals, including humans, or from microorganisms. A sample collected from a water system or a human body may be used directly without isolation of a nucleic acid if the cell-containing fluid or a body fluid, such as blood, may be treated with an alkaline solution, such as NaOH, to obtain cell lysates containing nucleic acids released from the cells. Then, a mixture for PCR may be added to the cell lysate to perform PCR. For example, if the amount of a sample is small, a significant amount of the sample may be lost during the process for isolating nucleic acids and the process may be costly and time consuming. Thus, it is advantageous that the sample itself is directly used in PCR.

According to an embodiment of the present invention, the alkali may be NaOH or KOH.

If an alkali is added to a sample that is to be subjected to PCR or a mixture for PCR, a nucleic acid from a sample in a reaction solution for PCR is changed into a single-stranded structure appropriate for PCR. Thus, PCR efficiency may be enhanced while omitting a pre-denaturation step that is typically included in PCR, such as incubation of the reaction solution for PCR at a temperature of about 94° C. to about 96° C. for about 5 to about 10 minutes before PCR reaction, thereby substantially reducing the time required for the PCR. In addition, if the PCR is performed in the presence of an alkali, fewer primer dimers are generated, thereby enhancing PCR efficiency, and leading to improvement in LOD and intensity of fluorescence signals. Thus, the use of alkali in PCR enables accurate and rapid detection of a target nucleic acid in the sample with high sensitivity.

According to an embodiment of the present invention, a final concentration of the alkali in the reaction solution for PCR may be in a range of about 0.005N to about 0.02N.

Alkali is widely used in preparing nucleic acid for PCR. For example, a treatment with NaOH may be performed to lyse cells or to enhance PCR efficiency with respect to a template with a high GC ratio. However, in general, a sample including a nucleic acid that is pre-treated with NaOH, is then neutralized, and the nucleic acids are purified from the sample for use as the template in PCR. According to an embodiment of the present invention, the alkali is not removed, for example, by neutralization, prior to PCR; the PCR is performed with the alkali present in the reaction solution for PCR. If the concentration of the alkali in the reaction solution for PCR is lower than 0.005 N, the beneficial effect from inclusion of the alkali in the reaction solution for PCR is negligible, while if the concentration of the alkali is higher than 0.02 N, the nucleic acid template may be damaged and become inappropriate for PCR or PCR may be inhibited by metal ions from alkali.

According to an embodiment of the present invention, the mixture for PCR may be a ×2 to ×10 mixture.

According to an embodiment of the present invention, the alkali may be NaOH, and the final concentration of NaOH in the reaction solution for PCR may be 0.01N.

According to an embodiment of the present invention, the PCR may be performed without a pre-denaturation step.

The term "pre-denaturation step" used herein refers to a step of incubating a template for PCR at a denaturation temperature of about 94 to about 96° C. for about 5 to about 10 minutes in order to sufficiently denature the template into single strands for PCR, before initiation of PCR.

According to an embodiment of the present invention, the PCR may be real-time PCR.

The term "real-time PCR (RT-PCR)" used herein refers to a method in which an increase in PCR products in each cycle of PCR is observed in real time by detecting and quantifying a fluorescent material that reacts with the PCR product in a sample. Compared to a traditional PCR method in which a PCR product is identified on a gel following electrophoresis of the reaction solution for PCR after completion of PCR, RT-PCR does not require electrophoresis, has high accuracy and sensitivity and high reproducibility. In particular, RT-PCR can be used as an automated diagnosis method in which amplification of a specific gene is identified, and also enables accurate quantification of target DNA and RNA (Mackay I M, Arden K E, Nitsche A. 2002. Real-time PCR in virology. *Nucleic Acids Res.* 30(6):1292-1305). In the case of a traditional quantitative PCR, the amount of DNA exponentially amplified prior to its saturation is measured. In RT-PCR, the amount of a sample at the initial reaction phase where exponential amplification occurs is represented as the number of cycles (Ct) at which an exponential increase in the fluorescent reporter begins to be detected. Thus, RT-PCR is a more accurate quantitative method and can be used to assay PCR in real-time. In RT-PCR, a primer may be labeled with a detectable label, or a separate labeled probe may be used. The detectable label refers to a compound, a biomolecule, or a biomolecule mimetic, which can be connected, bound, or attached to a primer or probe to identify the density, concentration, or amount thereof using a conventional method. Examples of a detectable label may be a commercially available fluorescence marker, a luminescent material, a biological luminescent material, and an isotope, but are not limited thereto. A fluorescence marker is most widely used as a detectable label and examples of the fluorescence marker include FAM, VIC, TAMRA, JOE, ROX, NED, HEX, TET, SYBR Green, Cy3, Texas Red, and Cy5™. The labeling method may be an intercalative method or a TaqMan™ probe method. In an intercalative method, an intercalative reagent (e.g., the intercalators: SYBR Green I, ethidium bromide (EtBr), etc.), which binds to a double-stranded DNA to emit fluorescent light, is added to a reaction solution for PCR and fluorescent light generated simultaneously with the amplification is detected. In the intercalative method, the intercalator binds to a double-stranded DNA generated by PCR to emit fluorescent light and the intensity of the fluorescent light is detected to measure the amount of amplification product. In a TaqMan™ probe method, an oligonucleotide (TaqMan™ probe) having a fluorescence marker (e.g., 6-carboxyfluorescein (FAM) etc.) at its 5' end and a quencher, such as tetramethylrhodamine (TAMRA), at its 3-' end is added to a reaction solution for PCR. According to this method, although the TaqMan™ probe is specifically hybridized with a template DNA in an annealing step, generation of fluorescent light is suppressed by the quencher in the probe. In an extension step, only the TaqMan™ probe hybridized with the template is digested by the 5'→3' exonuclease activity of Taq DNA polymerase and a fluorochrome is released from the probe and liberated from the suppression of the quencher, thereby emitting fluorescent light.

According to an embodiment of the present invention, RT-PCR is performed with high efficiency and high sensitivity without a pre-denaturation step and 1 or 2 copies of target nucleic acid in a sample may be detected within 10 minutes. The presence of alkali in a reaction solution for PCR enables a pre-denaturation step to be skipped and increases the reaction efficiency. Thus, for example, presence of a target material in a trace amount of a sample may be identified within a short time period by performing an appropriate number of cycles, each of which may consist of 1 second at 95° C. and 5 seconds at 60° C. (ramp rate: 30° C./sec).

According to an embodiment of the present invention, the method also suppresses generation of primer dimers in PCR. Thus, sensitivity of PCR may be significantly improved. If an appropriate concentration of alkali, such as NaOH, is included in a reaction solution for PCR, generation of primer dimers is decreased and thus PCR efficiency is enhanced, thereby improving LOD and the intensity of fluorescence signals. Methods used to suppress generation of primer dimers in PCR, such as strengthening stringency may lower PCR efficiency. However, the addition of alkali to a reaction solution for PCR suppresses generation of primer dimers while enhancing PCR efficiency.

Another aspect of the present invention provides a composition for high efficiency and high sensitivity PCR (PCR composition), including alkali and a mixture for PCR.

The term "high efficiency and high sensitivity PCR" used herein refers to PCR which shows higher efficiency and sensitivity than a traditional or conventional PCR. For example, the high efficiency and high sensitivity PCR may be a PCR which is conducted in a reaction solution including alkali, such as NaOH.

According to an embodiment of the present invention, the alkali may be NaOH or KOH.

According to an embodiment of the present invention, a final concentration of the alkali in the PCR composition may be in a range of about 0.005N to about 0.02N.

According to an embodiment of the present invention, the alkali may be NaOH, and a final concentration of NaOH in the PCR composition may be 0.01N.

If the concentration of the alkali in the PCR composition is lower than 0.005 N, the effect from the inclusion of alkali is negligible, and if the concentration of the alkali in the PCR composition is higher than 0.02 N, a nucleic acid as a template may be damaged and be inappropriate for PCR, or PCR may be inhibited by metal ions from alkali. If an appropriate concentration of alkali, such as NaOH, is included in the PCR composition, generation of primer dimers is decreased and thus PCR efficiency is enhanced, thereby leading to improvement in LOD the intensity of fluorescence signals. Accordingly, compared to a traditional mixture for PCR, the PCR composition including alkali enables PCR to be conducted with high-efficiency and high-sensitivity.

According to an embodiment of the present invention, the PCR composition may be used to prepare a reaction solution for RT-PCR that does not include a pre-denaturation step. Compared to a traditional PCR having a reaction time of 40 minutes to 50 minutes, a PCR composition according to an embodiment of the present invention enables a sample including less than 10 copies of a target nucleic acid to be detected and quantified by rapid PCR within 10 minutes.

One or more embodiments of the present invention will be described in further detail with reference to the following examples. These examples are for illustrative purposes only and are not intended to limit the scope of the embodiments of the present invention.

Example 1

Effects of Inclusion of NaOH in Reaction Solution for PCR on PCR Efficiency and Sensitivity Effects of inclusion of NaOH in a reaction solution for PCR on the efficiency and sensitivity of PCR were studied.

A fragment of the gene Sa442 (NCBI Accssion No. AF033191) set forth in SEQ ID. NO: 1 and that of the nuc gene (NCBI Accssion No. NC_002758.2) set forth in SEQ ID. NO: 2, which are commonly present in a Methicillin Resistant Staphylococcus aureus (MRSA) strain and a Methicillin Susceptible Staphylococcus aureus (MSSA) strain, were amplified by RT-PCR using primers designed by ABI (US) and TaqMan™ probes, both shown in Table 1 below.

TABLE 1

| | Sequence |
|---|---|
| Sa442 forward primer | 5'-GTT GCA TCG GAA ACA TTG TGT T-3' (SEQ ID. NO: 3) |
| Sa442 reverse primer | 5'-ATG ACC AGC TTC GGT ACT ACT AAA GAT-3' (SEQ ID. NO: 4) |

TABLE 1-continued

| | Sequence |
|---|---|
| Sa442 Taqman probe | 5'-TGT ATG TAA AAG CCG TCT TG-3' (SEQ ID. NO: 5) |
| nuc forward primer | 5'-TGC GAC ATT AAT TAA AGC GAT TG-3' (SEQ ID. NO: 6) |
| nuc reverse primer | 5'-GTC TGA ATG TCA TTG GTT GAC CTT-3' (SEQ ID. NO: 7) |
| nuc Taqman probe | 5'-TGG TGA TAC GGT TAA ATT-3' (SEQ ID. NO: 8) |

RT-PCR was performed using a TMC_2000 (Samsung electronics Co., Ltd; ramp rate of 4° C./sec. and 2.2° C./sec.) Compositions of the reaction solution for PCR are shown in Table 2 below.

TABLE 2

| Component | Volume | Final Concentration |
|---|---|---|
| 10x Z-Taq buffer solution | 0.2 μl | 1x |
| 25 mM dNTP | 0.16 μl | 2 mM |
| Taq polymerase | 0.02 μl | 0.05 U |
| 50 mM forward primer | 0.04 μl | 1 μM |
| 50 mM reverse primer | 0.04 μl | 1 μM |
| 20 mM probe | 0.04 μl | 0.4 μM |
| Water | 0.5 μl | — |
| gDNA | 1 μl | — |

Genomic DNA (gDNA) for MSSA ATCC BAA 1718 (GeneBank: AASB02000000) was purchased from ATCC (American Type Culture Collection, Catalog No. BAA-1718D-5). The number of gene copies in the sample was measured before using the DNA using a spectrophotometer and a quantitative fluorescence method.

1-1. Pre-Denaturation vs. NaOH

In order to identify the effects of addition of NaOH to a reaction solution for PCR, threshold cycle (Ct) values were measured for PCR with NaOH addition to the PCR reaction solution and for PCR performed with a pre-denaturation step. To do this, PCR was performed under the following three conditions and the results were compared with each other.

(1) Inclusion of pre-denaturation step: A quantified nucleic acid sample was dissolved in distilled water. After assembly of the reaction solution for PCR, the reaction solution for PCR was incubated at a temperature of 95° C. for 5 minutes as a pre-denaturation step. Then, PCR was performed on the reaction solution for PCR for 45 cycles of denaturation at 95° C. for 1 seconds and extension at 60° C. for 5 seconds.

(2) Non-inclusion of pre-denaturation step: A quantified nucleic acid sample was dissolved in distilled water. After assembly of the reaction solution for PCR, PCR was performed on the reaction solution for PCR for 45 cycles of denaturation at 95° C. for 1 second and extension at 60° C. for 5 seconds without the 5-minute pre-denaturation step at 95° C.

(3) Inclusion of 0.02N NaOH: A quantified nucleic acid sample was dissolved in 0.02N NaOH solution. After assembly of the reaction solution for PCR, PCR was performed on the reaction solution for PCR for 45 cycles of denaturation at 95° C. for 1 second and extension at 60° C. for 4 seconds without the 5-minute pre-denaturation step at 95° C.

FIG. 1A and Table 3 below show the PCR results.

TABLE 3

| Gene copy number: 20 | Average Ct value | Standard deviation | PCR Efficiency |
|---|---|---|---|
| Inclusion of pre-denaturation | 34.40 | 0.52 | 93% |
| Non-inclusion of pre-denaturation | 35.87 | 0.85 | 82% |
| Addition of 0.02N NaOH | 33.59 | 0.16 | 95% |

When the gDNA was denatured in a pre-denaturation step, the Ct value was decreased by about 1.5 compared to the Ct value determined when no pre-denaturation step was included in the PCR protocol. Addition of 0.02N NaOH to the template solution resulted in a Ct value that was decreased by about 2.3 compared to the Ct value determined when no pre-denaturation step was included in the PCR protocol.

Figure 1B:
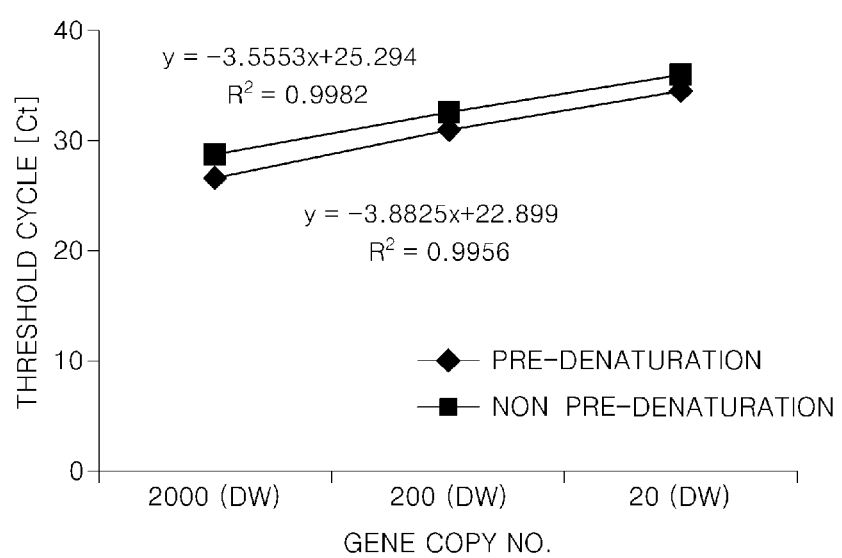
FIG. 1B is a graph of Ct values as a function of gene copy number for PCR with or without a pre-denaturation step.

The effect of template copy number was compared for the PCR protocol with the pre-denaturation step and the PCR protocol without the pre-denaturation step. The results are shown in FIG. 1B. Inclusion of the pre-denaturation step in the protocol decreased the Ct value at each copy number tested compared to that measured to the protocol without the pre-denaturation step. Although inclusion of the pre-denaturation step decreased Ct, at a low concentration of the sample, PCR efficiency was reduced. PCR efficiency was evaluated by inputting a slope obtained using a reference curve by DNA concentration to the following equation:

PCR efficiency=(10^(−1/slope))−1)×100).

1-2. Optimal NaOH Concentration

In order to determine the effect of NaOH concentration on PCR Ct value, PCR was performed under the same conditions as in Section 1-1 (3), except that $2 \times 10^4$ copies of the gene were dissolved in 0N, 0.01N, 0.02N, 0.03N, and 0.05N NaOH, respectively, prior to preparing the reaction solution for PCR. In these experiments, the reaction solution for PCR was prepared from a x2 mixture for all PCR components except the template added to an equal volume of the template solution. The Ct values determined in these experiments are presented in FIG. 2 and Table 4 below.

Figure 2:
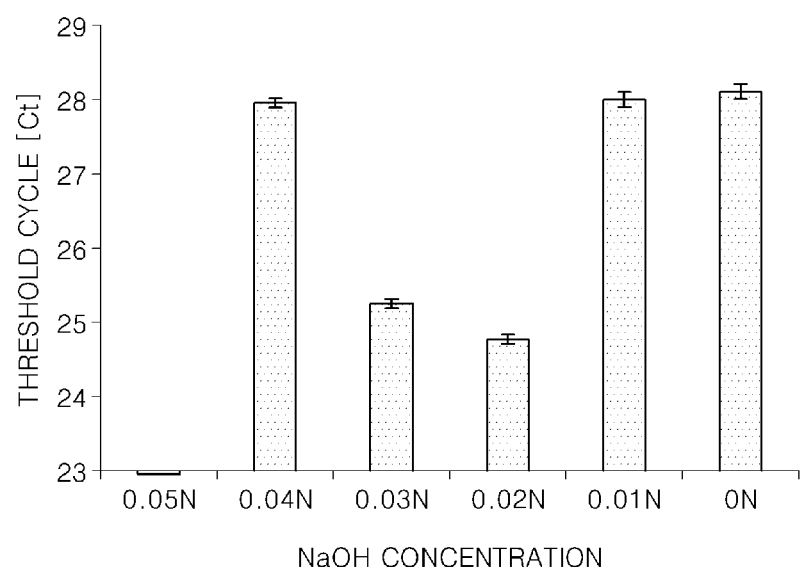
FIG. 2 is a histogram showing Ct values as a function of NaOH concentration in the template solution for PCR.

As illustrated in FIG. 2 and Table 4 below, when 0.01 to 0.04N NaOH was added to the template solution, the Ct value decreased compared to when NaOH was not added.

TABLE 4

| NaOH concentration in template solution | Average Ct value | Standard deviation |
|---|---|---|
| 0.05N | — | — |
| 0.04N | 27.97 | 0.05 |

TABLE 4-continued

| NaOH concentration in template solution | Average Ct value | Standard deviation |
|---|---|---|
| 0.03N | 25.26 | 0.05 |
| 0.02N | 24.76 | 0.04 |
| 0.01N | 28.00 | 0.10 |
| 0N | 28.22 | 0.10 |

The results above show that the Ct value is smallest when the final concentration of NaOH in the reaction solution for PCR is 0.01N, i.e., when the concentration of NaOH in the template solution is 0.02N.

Figure 3:
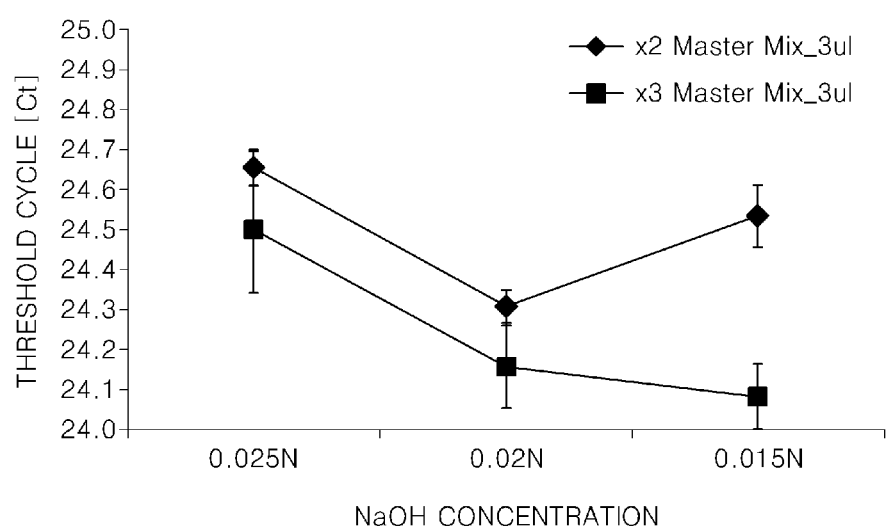
FIG. 3 is a graph of Ct values as a function of NaOH concentration in the PCR for two different PCR master mixes.

In addition, ×2 and ×3 Master Mixes were used as mixtures for PCR, and $6 \times 10^4$ template nucleic acids were amplified by RT-PCR in the presence of 0.015 to 0.025N NaOH in a 3 μl chip (TMC_2000) in order to define an optimal NaOH concentration. FIG. 3 and Table 5 below show that the Ct value is smallest when a final concentration of NaOH in a reaction solution for PCR is in a range of about 0.005N to about 0.01N.

TABLE 5

| Final NaOH concentration in respective master mix | x2 Master Mix_3 μl | | x3 Master Mix_3 μl | |
|---|---|---|---|---|
| | Average Ct value | Standard deviation | Average Ct value | Standard deviation |
| 0.025N | 24.65 | 0.04 | 24.50 | 0.16 |
| 0.02N | 24.31 | 0.04 | 24.16 | 0.10 |
| 0.015N | 24.53 | 0.08 | 24.08 | 0.08 |

1-3. Reaction Efficiency and Reaction Sensitivity of PCR

Effects of the inclusion of NaOH in a PCR reaction solution on PCR reaction rate and LOD were studied. To do this, the template samples were dissolved in distilled water or 0.02N NaOH, respectively. Then, the reaction solution for PCR was made with the template solution which was prepared by diluting 60 ng/μl via 1:10 serial dilutions to $2 \times 10^5$–$2 \times 10^0$ templates, and PCR was performed.

Figure 4A:
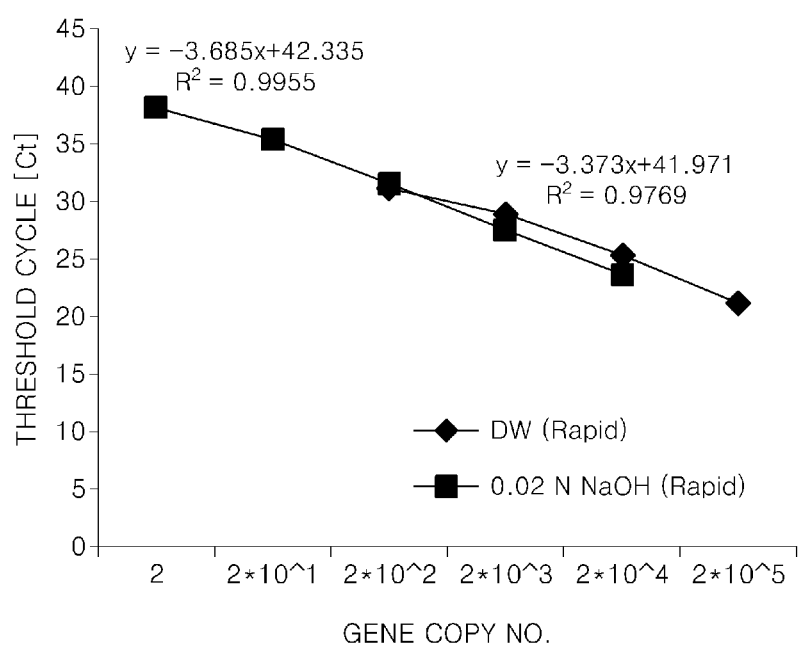
FIG. 4A is a graph of Ct values for Rapid PCR as a function of gene copy number that shows the limit of detection (LOD) of Rapid PCR in a sample in 0.02N NaOH and a sample in distilled water, respectively.
Figure 4B:
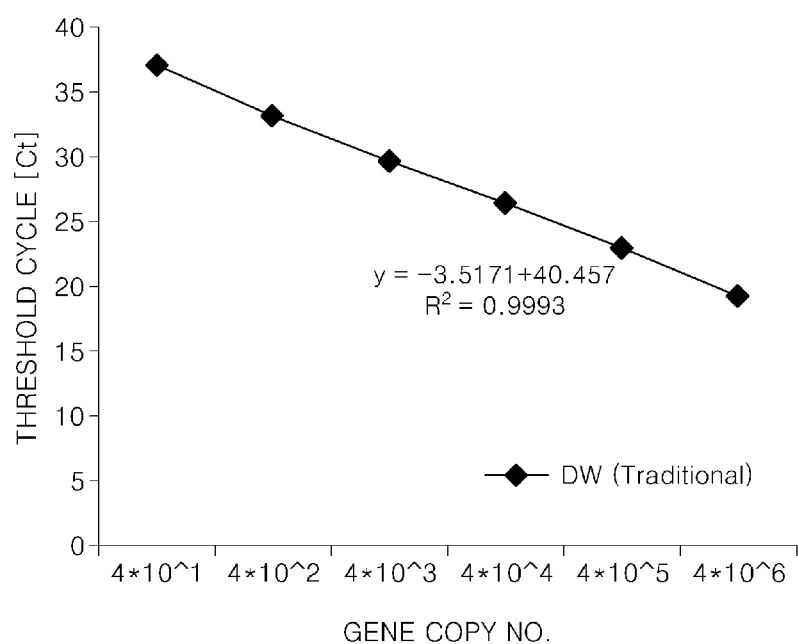
FIG. 4B is a graph of Ct values for traditional PCR as a function of gene copy number that shows the LOD of traditional PCR in a sample in distilled water.

Rapid PCR and traditional PCR, respectively, were performed under the following conditions: 95° C., 1 second/60° C., 5 seconds (ramp rate of 30° C./sec.) and 95° C., 10 seconds/60° C., 60 seconds (ramp rate of 4° C./sec., 2.2° C./sec.). The temperature cycle was repeated 45 times in order to detect a small number of gene copies. FIG. 4A presents Ct values determined by rapid PCR while FIG. 4B presents Ct values determined by traditional PCR.

(1) Nucleic Acid Sample

As illustrated in FIG. 4A, when the nucleic acid sample was dissolved in 0.02N NaOH, Ct value for rapid PCR as a function of gene copy number was linear from $2 \times 10^4$ copies down to two copies of the gene in the sample. Additionally, PCR was performed with high efficiency and high sensitivity. Rapid PCR could be completed within 10 minutes with an efficiency of 86% or higher, and with an LOD of 1 to 2 copies.

When the nucleic acid sample was dissolved in distilled water (DW, in FIG. 4A), the LOD of rapid PCR was $10^2$ copies.

As illustrated in FIG. 4B, Ct value for traditional PCR as a function of gene copy number was linear from $4 \times 10^6$ copies down to 40 copies of the gene in the sample dissolved in distilled water, indicating that LOD of traditional PCR was about 40 copies. Additionally, the traditional PCR took 50 minutes for completion.

(2) Cell Sample 0.02N NaOH was added to a sample of Staphylococcus aureus (MSSA), a gram-positive bacterium, without isolation of the nucleic acid from the sample to yield a final concentration of 0.02N NaOH in the sample. Then the sample was treated with ultrasonic waves for 5 minutes. A reaction solution for PCR having the composition shown in Table 2 above was prepared with this lysed cell sample.

The following PCR cycle conditions were performed on the reaction solution for PCR, without a pre-denaturation step: 45 cycles of 1-second denaturation at 95° C. and 5-second extension at 60° C. With the addition of NaOH to the cell sample, the nucleic acid was released from the cell into the sample, the structure of the nucleic acid was loosened, and generation of primer dimers was suppressed, thereby enhancing PCR efficiency. The results of PCR on reaction solutions prepared from samples of various initial numbers of cells are shown in Table 6 below.

TABLE 6

| MSSA cell count (colony forming units/volume) | Average Ct value | Standard deviation |
|---|---|---|
| $10^3$ | 31.8 | 0.3 |
| $10^4$ | 29.2 | 0.3 |
| $10^5$ | 25.6 | 0.6 |

Example 2

Effects of NaOH Addition to Reaction Solution for PCR on Generation of Primer Dimers During PCR, annealing may occur between primers and when amplification is performed, primer dimers may be generated, reducing PCR efficiency and detection sensitivity. In the present example, effects of NaOH addition on generation of primer dimers were identified.

Figure 5A:
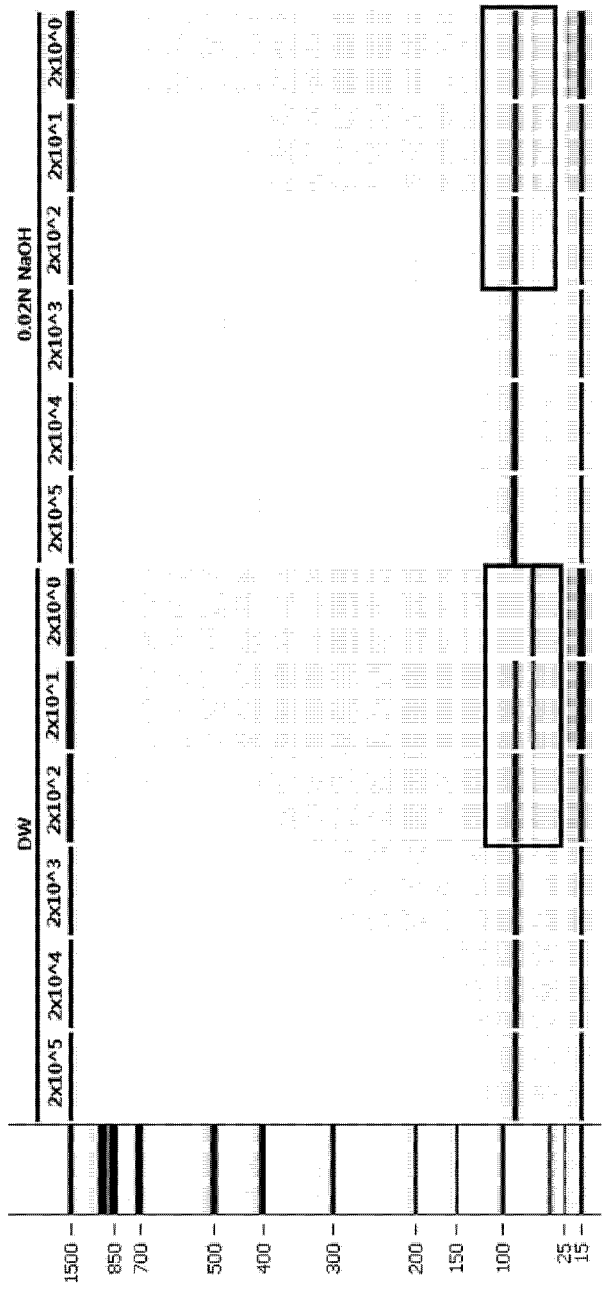
FIG. 5A is a photographic image of a gel electrophoresis separation showing the effect of NaOH on generation of primer dimers in a real-time PCR for amplifying a Sa442 fragment using a ×2 master mix.
Figure 5B:
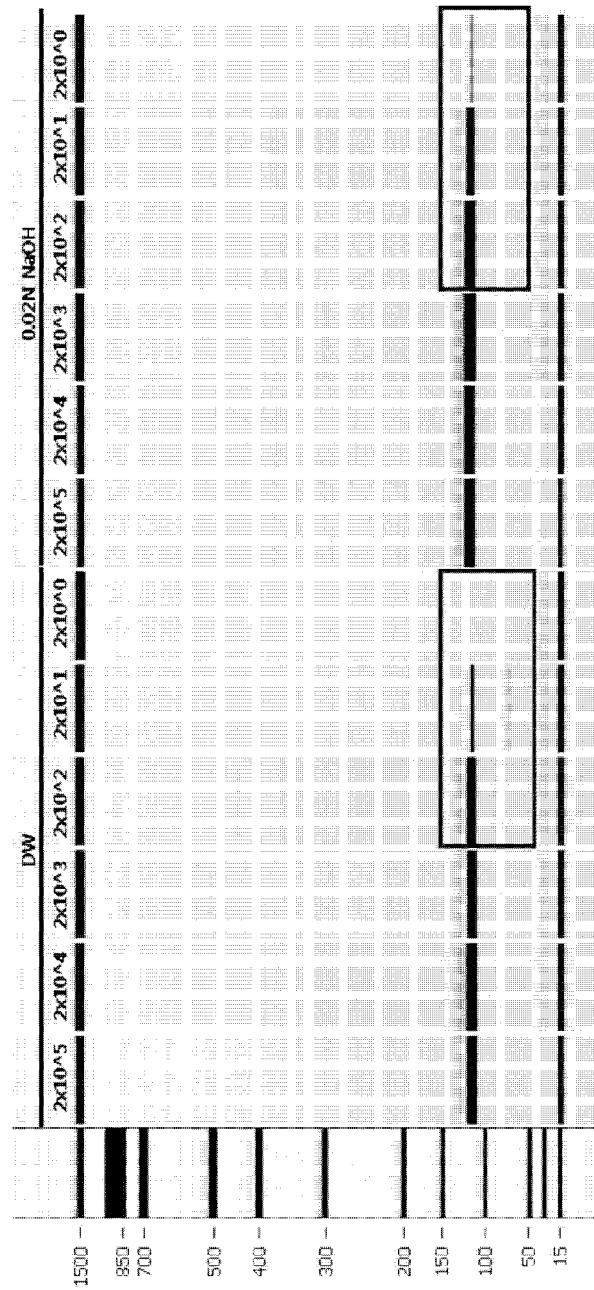
FIG. 5B is a photographic image of a gel electrophoresis separation showing the effect of NaOH on generation of primer dimers in a real-time PCR for amplifying a Nuc gene using a ×2 master mix.

Staphylococcus aureus gDNA including the Sa442 gene fragment and the Nuc gene was dissolved in distilled water or 0.02N NaOH at various concentrations in terms of gene copy numbers. The gDNA solution was added, in equal volume, to a ×2 mixture for PCR to prepare a reaction solution for PCR. PCR was then performed using the following thermal cycles: 45 cycles of 1 second-denaturation at 95° C. and 4-second extension at 60° C. The amplification product was analyzed for the amount of primer dimers generated using a Lab-chip on an Agilen Bioanalyzer 2000. FIGS. 5A and 5B present images of the electrophoretic separation performed on the Lab-chip. A decrease in the amount of primer dimers generated was observed when a nucleic acid sample was dissolved in 0.02N NaOH. When NaOH was added, the number of primer dimers was significantly decreased at concentrations below $10^2$ copies (compare the two boxed regions of FIG. 5A). The signal intensity of the target product was improved at a given copy numer, and the signal to noise ratio was increased, thereby improving LOD According to an embodiment of the present invention, a method of enhancing PCR efficiency and sensitivity makes it possible to detect a target microorganism, cell or gene in a sample with high efficiency and high sensitivity.

The terminology used herein is for the purpose of describing particular embodiments only and is not intended to be limiting of the invention. The terms "a" and "an" do not denote a limitation of quantity, but rather denote the presence of at least one of the referenced item. The terms "comprising", "having", "including", and "containing" are to be construed as open-ended terms (i.e. meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. No language in the specification should be construed as indicating any non-claimed element as essential to the practice of the invention as used herein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A method of enhancing reaction efficiency and sensitivity of polymerase chain reaction (PCR), the method comprising:
   preparing a biological sample and a mixture for PCR;
   adding alkali to at least one of the biological sample and the mixture for PCR, wherein the alkali is selected from the group consisting of NaOH or KOH,
   mixing the biological sample and the mixture for PCR to prepare a reaction solution for PCR having a final alkali concentration in a range of about 0.005N to about 0.02N; and
   performing the PCR on the reaction solution for PCR.

2. The method of claim 1, wherein the biological sample is a cell, a body fluid, or a nucleic acid.

3. The method of claim 1, wherein the mixture for PCR is a 2× to 10× mixture.

4. The method of claim 1, wherein the alkali is NaOH and a final concentration of NaOH in the reaction solution for PCR is 0.01N.

5. The method of claim 1, wherein the PCR is performed without a pre-denaturation step.

6. The method of claim 1, wherein the PCR is a real time-PCR.

7. The method of claim 1, wherein the method leads to reduction in generation of primer dimers.

8. The method of claim 1, wherein the alkali is NaOH.

9. The method of claim 1, wherein the alkali is KOH.

* * * * *